(12) United States Patent
Szczepanski et al.

(10) Patent No.: US 9,326,880 B2
(45) Date of Patent: May 3, 2016

(54) DEVICE AND METHODS FOR TREATMENT OF STATIC ANKLE PLANTAR FLEXION

(71) Applicants: Jeffrey A Szczepanski, Traverse City, MI (US); Fredrick P Schoville, Brighton, MI (US)

(72) Inventors: Jeffrey A Szczepanski, Traverse City, MI (US); Fredrick P Schoville, Brighton, MI (US)

( * ) Notice: Subject to any disclaimer, the term of this patent is extended or adjusted under 35 U.S.C. 154(b) by 113 days.

(21) Appl. No.: 14/150,159

(22) Filed: Jan. 8, 2014

(65) Prior Publication Data

US 2015/0190263 A1 Jul. 9, 2015

(51) Int. Cl.
*A61F 5/00* (2006.01)
*A61F 5/01* (2006.01)

(52) U.S. Cl.
CPC ....... *A61F 5/0127* (2013.01); *A61F 2250/0006* (2013.01)

(58) Field of Classification Search
CPC ........ A43B 21/26; A43B 21/28; A43B 21/37; A43B 21/42; A43B 13/12; A43B 13/141; A43B 13/16; A43B 23/027; A43B 3/126; A43B 5/04; A43B 5/0427; A43B 5/0472; A43B 11/00; A43B 23/24; B08B 15/00; B08B 15/002; B65D 85/68; A61F 5/0113; A61F 5/05; A61F 5/0585; A61F 2007/0047; A61F 2007/0096; A61F 5/0111; A61F 7/02; A63B 2023/006; A63B 2071/0694; A63B 21/00043
USPC ...................................................... 602/23–28
See application file for complete search history.

(56) References Cited

U.S. PATENT DOCUMENTS

| | | | | |
|---|---|---|---|---|
| 5,399,155 A | * | 3/1995 | Strassburg et al. | 602/28 |
| 5,486,157 A | * | 1/1996 | DiBenedetto | 602/27 |
| 8,864,696 B1 | * | 10/2014 | Frierson | 602/23 |

* cited by examiner

*Primary Examiner* — Michael Brown
(74) *Attorney, Agent, or Firm* — Mitchell Law PLLC; Matthew W. Mitchell

(57) ABSTRACT

Device embodiments and methods for using same are disclosed for treatment of static ankle plantar flexion. The device includes a sock configured to contain a patient's foot, the sock having a loop at an upper portion and a mechanical link coupled to the loop. The device further includes an adjustable plate, and an adjustable strap that is configured to selectively attach to the mechanical link. A cavity is formed by the sock and the adjustable strap that is configured to hold the adjustable plate when the strap is engaged to the mechanical link.

13 Claims, 5 Drawing Sheets

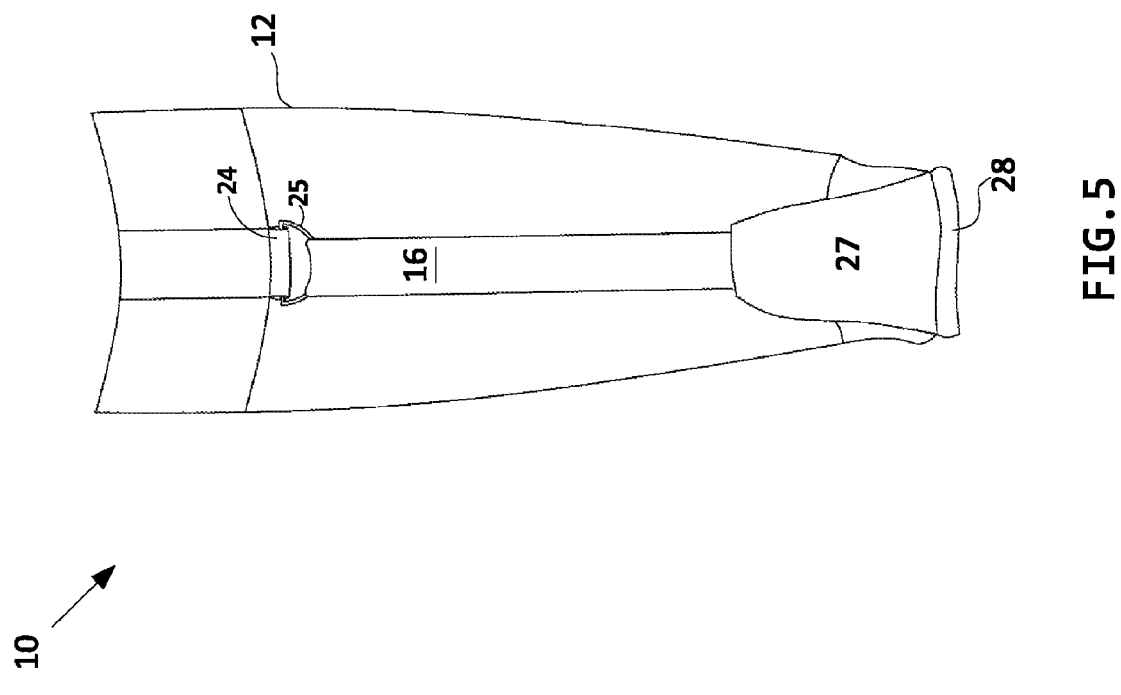

DEVICE AND METHODS FOR TREATMENT OF STATIC ANKLE PLANTAR FLEXION

TECHNICAL FIELD

This disclosure relates to medical devices and treatment methods, and more particularly to a device and methods for treatment of static ankle plantar flexion.

BACKGROUND

The statements in this section merely provide background information related to the present disclosure and may not constitute prior art.

The human foot is generally divided into the dorsal (top) and plantar (bottom) portions. On the plantar surface there are several layers of muscle, bone, tendon, fascia and neurovascular structures. The plantar fascia is a normal anatomical structure with two main bands; a medial and lateral. The plantar fascia sits beneath the subcutaneous tissue and superficial to the deep foot intrinsic muscles. The plantar fascia can sometimes be described as an aponeurosis. In the posterior ankle a normal anatomical structure exists that is commonly referred to as the Achilles tendon. This tendon is formed by three separate muscles-gastrocnemius, soleus and plantaris together create the Achilles tendon.

A common foot condition/ailment exists that causes intense heel or arch pain. It can be referred to as plantar fasciitis, heel spur, heel spur syndrome or plantar fibromas. These syndromes usually develop from overuse and commonly cause pain which is referred to as post static dyskinesia, i.e., pain after rest. An intense inflammation of the plantar fascia will result in mild to severe pain, occurring in the heel or arch, although varying patient-to-patient. On a rare occasion a patient can have a different etiology for their symptoms not limited to calcaneal stress fracture, tarsal tunnel syndrome, calcaneal branch nerve impingement, tendonitis, neoplasm growth or deep vein thrombosis.

Another common ailment exists that is referred to Achilles tendonitis. This syndrome will create pain in the back of the ankle. Patients commonly will experience pain along the tendon either at "mid substance" which is referred to as 3-5 cm above its insertion into the calcaneus. The patient can also experience pain directly at the insertion of the Achilles into the calcaneus. Quite often, localized swelling will develop near the painful area. Although, different etiologies can cause pain in the back of the ankle that are not limited to Achilles tendon rupture, gout, deep vein thrombosis or the ostrigonum syndrome.

Many known treatments exist for the above syndromes. With plantar fasciitis, common treatments include NSAIDs, physical therapy, arch support/orthotics, cast immobilization, corticosteroid injection, surgery and splinting devices. With Achilles tendinitis common treatments include NSAIDs, heel lifts, cast or boot immobilization and physical therapies. Posterior leg and foot stretching devices are commonly accepted forms of treatment for plantar fasciitis, calcaneal spur syndrome and Achilles tendonitis.

Many current devices can cause significant discomfort from overstretching foot structures. These existing devices as it relates to plantar fasciitis/calcaneal spur's, e.g., heel spur's, pull directly on the patient's foot, causing undue stress and pressure including on the upper portion of the foot resulting in discomfort to the patient. Further, many patients have conditions in the foot or ankle which limits her ability to stretch. Conditions such as degenerative joint disease can experience increased pain if overstretching exists.

Therefore, a need exists for a device and method for treating static ankle plantar flexion in a manner that reduces discomfort as compared to known methods and devices including a need to enable a patient to selectively and precisely control the degree to stretching.

SUMMARY

Devices and methods are disclosed for treating static ankle plantar flexion. The device includes a sock configured to contain a patient's foot, the sock having a loop at an upper portion and a mechanical link coupled to the loop. The device further includes an adjustable plate, and an adjustable strap that is configured to selectively attach to the mechanical link. A cavity is formed by the sock and the adjustable strap that is configured to hold the adjustable plate when the strap is engaged to the mechanical link.

One method disclosed herein for treating static ankle plantar flexion includes providing a calf sock having a first opening for the patient's foot and a second opening for an adjustable plate, adjusting an angle of the plate, engaging an adjustable plate with the underside of the patient's foot, and applying tension between a top portion of the calf sock and the adjustable plate using a flexible strap to support a patient's foot structures at a slight dorsiflexion.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which:

FIG. 5 shows a front view of the medical device when deployed in use, in accordance with the present disclosure.

DETAILED DESCRIPTION

Figure 1:
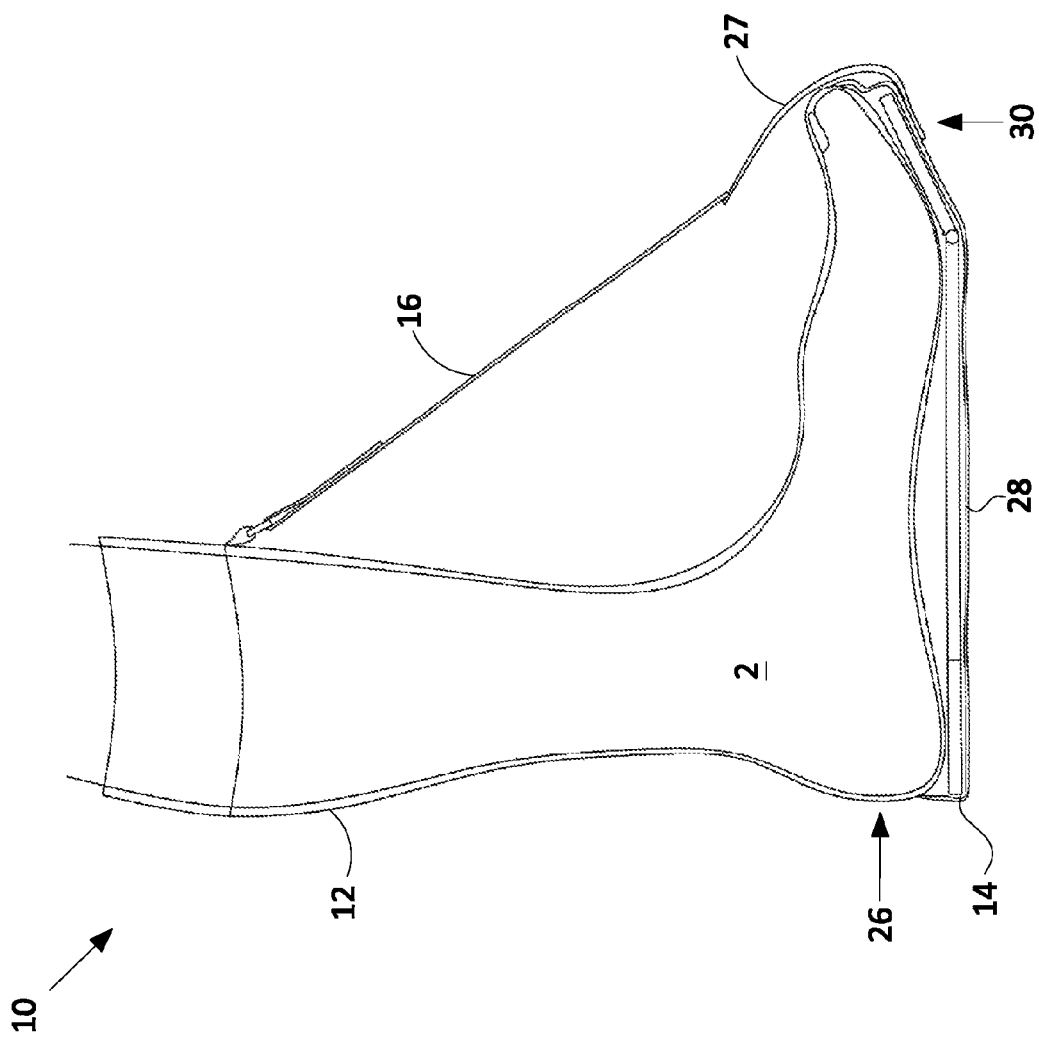
FIG. 1 shows a cross-sectional side view of a medical device on a patient's foot, in accordance with the present disclosure.

Referring now to the drawings, wherein the depictions are for the purpose of illustrating certain exemplary embodiments only and not for the purpose of limiting the same, FIG. 1 shows a device 10 for treating and preventing ankle plantar flexion of a patient's foot 2. The device 10 includes a calf sock 12, an adjustable plate 14, and an adjustable strap 16. The adjustable strap 16 may be integrally connected to the sock 12 at various points. The adjustable plate 14 is preferably disposed into the device 10 via a slot formed of the sock 12 and the strap 16 as described herein below but may be integral thereof in one embodiment.

Figure 2A:
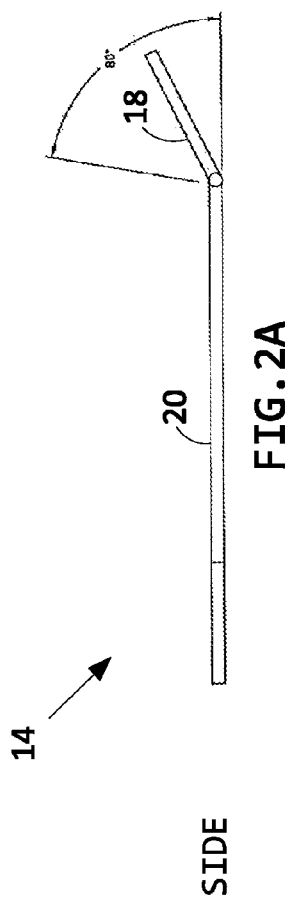
FIG. 2A is a side view of an adjustable plate of the medical device, in accordance with the present disclosure.
Figure 2B:
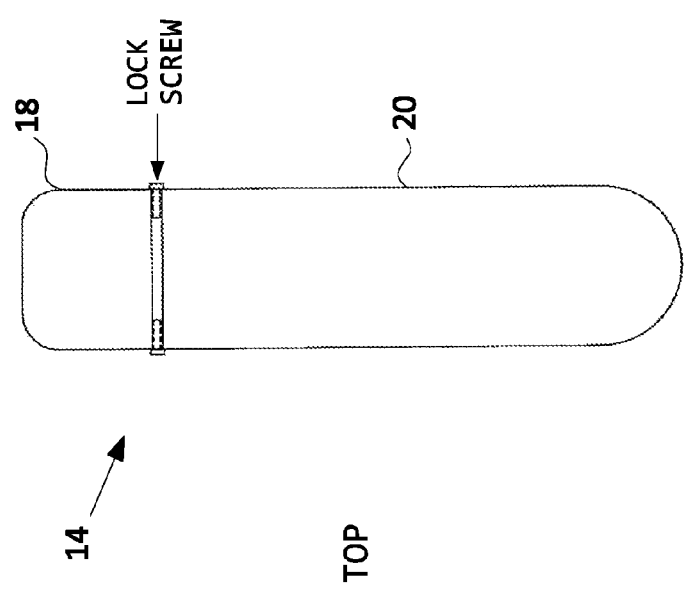
FIG. 2B is a top view of an adjustable plate of the medical device, in accordance with the present disclosure.

FIGS. 2A and 2B show an exemplary embodiment of the adjustable plate 14. FIG. 2A is a side view of the plate 14. FIG. 2B is a top view of the plate 14. The adjustable plate 14 is configured to be set and locked at user-selectable degrees, giving support to the foot when used. As FIGS. 2A and 2B show, the adjustable plate 14 may include a distal portion 18 and a proximal portion 20. The distal portion 18 is configured for arrangement by the toes of the foot while the proximal portion 20 is configured for arrangement by the heel and base of the foot. The distal and proximal portions 18 and 20 are preferrably rotably engaged along an axis. In one embodiment the distal and proximal portions 18 and 20 are mechanically connected using lock screws 19. One skilled in the art will recognize that one of any number of rotatably mechanical pivot connections may be used to attach the distal and proximal portions 18 and 20 including, e.g., bolts, tabs, snap fasteners, and pivot joints. The distal and proximal portions 18 and 20 may be formed or adapted for foot contours. In one embodiment, the distal and proximal portions 18 and 20 are selectively rotable about a predetermined range, e.g., from zero-degrees to 80-degrees. In operation, a user may rotate the portions to a desired angle and subsequently lock in the angle. An angle greater than zero-degrees is used to keep the toes in a slight dorsiflexion while not over stressing the remainder of the foot.

Figure 3:
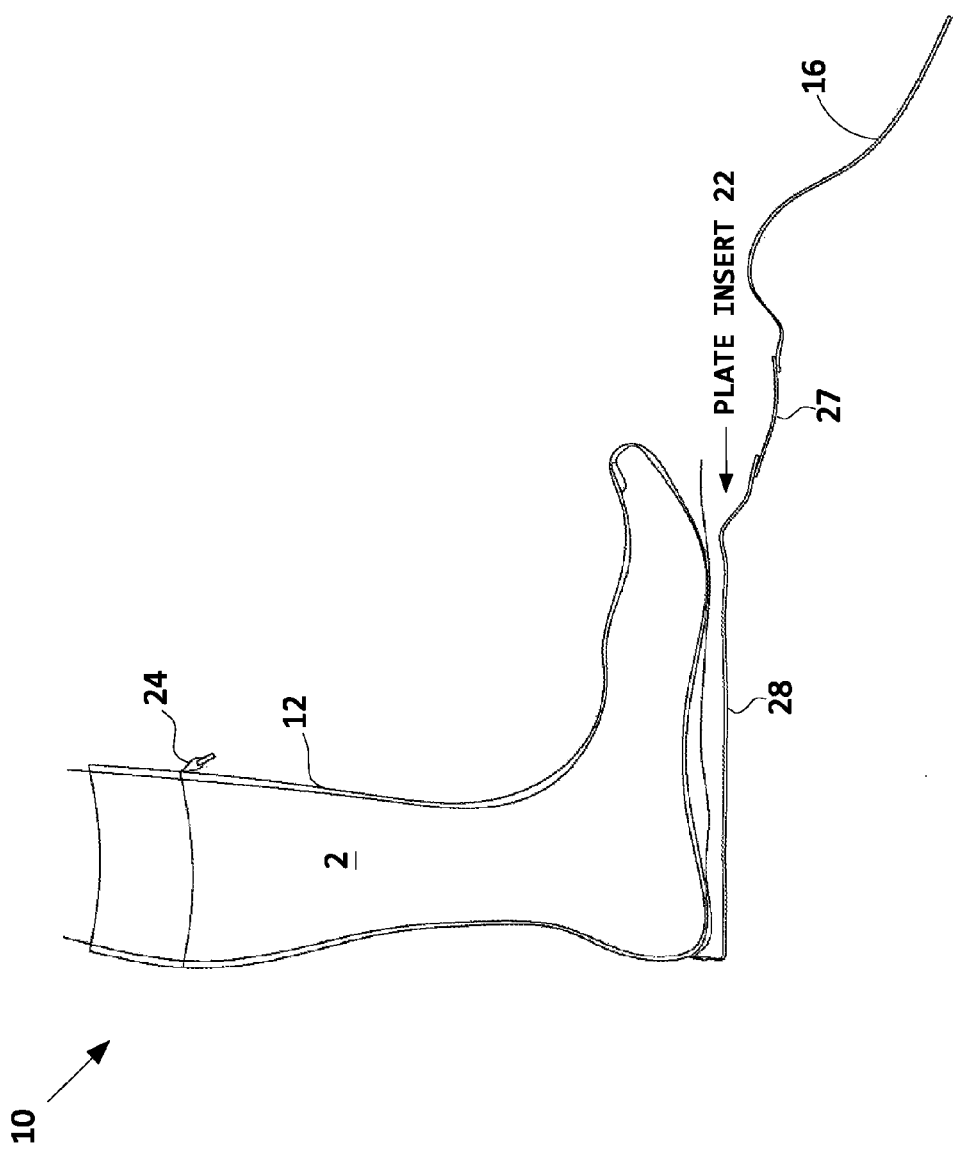
FIG. 3 shows a cross-sectional side view of the medical device depicting an opening configured to receive the adjustable plate, in accordance with the present disclosure.

FIG. 3 shows a cross-sectional side view of the medical device 10 on a patient's foot without the adjustable plate 14 illustrating a cavity or slot 22 configured to receive the plate 14. As FIG. 3 shows, the calf sock 12 includes a conventional cavity or opening for receipt of a foot 2 and a secondary opening 22 configured to receive and hold the plate 14. In one embodiment, the opening 22 may be formed by coverage of the strap 16 over the bottom of the sock 12. The sock 12 includes a strap attachment means 24 on an upper portion of the calf sock. The strap attachment means may be an integrated fabric loop configured to receive a mechanical fastener or link such as a 'D' ring 25. In one embodiment, the strap attachment means may be secured using a hook-and-loop fastener. In another embodiment, the strap attachment means may be sewn or otherwise secured to the sock 12. As FIG. 3 shows, the strap 16 may be attached to the bottom portion of the sock at area 26 to form the opening 22. In some embodiments, the opening 22 is integral to the sock and the strap 16 is connected to the sock at area 30.

Figure 4:
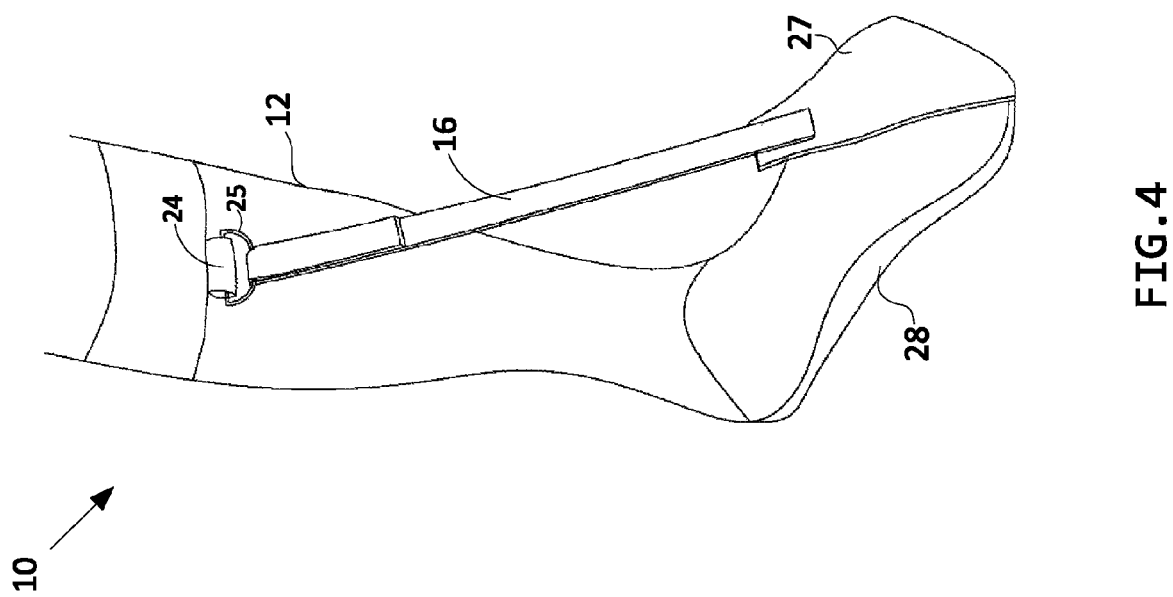
FIG. 4 shows a perspective view of the medical device illustrating an embodiment of the adjustable strap, in accordance with the present disclosure.

FIG. 4 shows a perspective view of the medical device 10 illustrating an embodiment of the adjustable strap 16 while in operation. As FIG. 4 shows, the strap 16 is attached to the sock 12 via a D-ring 25 which is connect to an integrated fabric loop 24 at a first end. At a second end, the strap 16 may be attached to a bottom portion of a distal plate covering portion 27 of the sock 12. The distal plate covering portion 27 may be sized and adapted to cover the distal plate portion 18 and to communicate tension from the strap 16 evenly along an axis of the distal plate 18. A proximate plate coving portion 28 is connected or integral with the distal plate covering portion 27. The portion 28 is configured to form the opening 22 from which to receive the plate 14. The strap 16 is preferably elastic to provide flexibility to the user. The strap 16 may include hook-and-loop material so that the length may be adjusted by the user.

FIG. 5 shows a front view of the medical device 10. As FIG. 5 shows, the plate 14 is held against a patient's foot by the proximate plate coving portion 28, when engaged. The proximate plate coving portion 28 covers the bottom portion of the device 10 while forming the opening 22 for the plate 14 as described herein above. The distal plate covering portion 27 covers the distal plate portion 18 of the plate and communicates tension forces from the strap 16 evenly along an axis preferably parallel with the row of a patient's toes.

When the strap 16 is passed thru the D-ring 25 and secured by means of a hook and loop assembly, the Plantar Fascia of a patient's foot can be maintained in the desired position set by the plate 14. When engaged, the strap 16 pulls on the plate 14 and not the foot, preventing temporary neuropraxia, sometimes referred to as "foot falling asleep" or "pins and needles" sensations.

When engaged, the medical device 10 can stretch or position the patient's toes upward without causing discomfort. The medical device 10 has the ability to be set at different angular positions via the adjustment plate and different tension settings by adjustment of the strap 16. These adjustments allow direct patient control of stretching, thereby empowering a patient to avoid or mitigate overstretching of the forefoot structures such as metatarsal phalangeal joints, plantar muscles and tendons and neurovascular structures. The amount of stretch will be directly controlled by patient's adjustment of the flexed plate 14. When used appropriately, the patient can increase the healing rates of plantar fasciitis, heel spur syndrome and Achilles tendonitis thereby reducing patient pain. The device 10 should not be used in a manner that could cause rupture of the plantar fascia or Achilles tendon.

The device 10 is primarily intended to be used at sleep or rest, reducing the pain of post-static dyskinesia. In some situations, the medical device 10 can be worn to bed by a patient without significant restrictions and will not interrupt normal sleep, thereby allowing for several hours of active passive stretching, increasing the healing rate and time and reducing overstress or strain of vital foot and ankle anatomical structures including heel spur symptoms.

When used in conjunction with other treatment protocols it can allow for the full reduction of many painful syndromes. As described hereinabove, the medical device 10 allows for both static and dynamic stretching of the plantar fascia and the Achilles tendon of the posterior lower leg and plantar foot structures. For patients suffering from damaged or overstressed forefoot structures such as metatarsal phalangeal joints, plantar muscles and tendons and neurovascular structures stretching has been shown to be an important part of the healing process. Further, the device 10 will allow for a prolonged reduction in pain from various conditions such as plantar fasciitis, calcaneal heel spur, heel spur syndrome and Achilles tendinitis.

The disclosure has described certain preferred embodiments and modifications thereto. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A medical device comprising:
    a sock configured to contain a patient's foot, the sock comprising a loop at an upper portion of the sock and a mechanical link coupled to the loop;
    an adjustable plate;
    an adjustable strap configured to selectively attach to the mechanical link; and
    a cavity formed by the sock and the adjustable strap and configured to hold the adjustable plate.

2. The medical device of claim 1, wherein the adjustable plate comprises a proximal portion and a distal portion, the proximal portion and the distal portion rotably engaged along an axis.

3. The medical device of claim 2, wherein the proximal portion and the distal portion are engaged about an axis to rotate between zero and 80-degrees about the axis.

4. The medical device of claim 2, wherein the proximal portion and the distal portion are engageable at a selected angle.

5. The medical device of claim 4, wherein the angle is selectable from a range of zero to 80-degrees.

6. The medical device of claim 2, wherein the proximal portion and the distal portion are engaged using lock screws.

7. The medical device of claim 1, wherein the adjustable strap includes a hook and loop assembly configured to engage the strap around the mechanical link.

8. The medical device of claim 1, wherein the strap comprises elastic material.

9. The medical device of claim 1, wherein the sock and the adjustable strap are integrally connected.

10. A medical device configured to support a patient's foot structures at a slight dorsiflexion, the device comprising:
   a calf sock comprising a first opening configured to contain a patient's foot and a second opening configured to receive an adjustable plate for engagement against an underside of the patient's foot;
   the adjustable plate comprising a proximal portion and a distal portion, wherein the proximal portion and the distal portion are connected along an axis via a lockable mechanical fastener;
   a loop integrally connected to the calf sock at an upper portion;
   a mechanical D-link coupled to the loop; and
   a strap configured to form the second opening, wherein the strap is partially comprised of flexible material and configured to selectively attach to the mechanical link using a hook and loop assembly.

11. The medical device of claim 10, wherein the proximal portion and the distal portion are engaged about an axis to selectively rotate between zero and 80-degrees about the axis.

12. The medical device of claim 10, wherein the proximal portion and the distal portion are engageable at a selected angle between zero to 80-degrees.

13. The medical device of claim 12, wherein the proximal portion of the adjustable plate may be adapted to engage contours of the underside of the patient's foot.

* * * * *